United States Patent [19]

Flohr

[11] Patent Number: 5,654,995
[45] Date of Patent: Aug. 5, 1997

[54] X-RAY COMPUTED TOMOGRAPHY APPARATUS

[75] Inventor: Thomas Flohr, Uehfeld, Germany

[73] Assignee: Siemens Aktiengesellschaft, Munich, Germany

[21] Appl. No.: 424,060

[22] Filed: Apr. 19, 1995

[30] Foreign Application Priority Data

Apr. 20, 1994 [DE] Germany .................... 44 13 689.7

[51] Int. Cl.⁶ .................................................. G01N 23/00
[52] U.S. Cl. .................................. 378/10; 378/4; 378/901
[58] Field of Search ................................ 378/10, 4, 901

[56] References Cited

FOREIGN PATENT DOCUMENTS 2 044 985  10/1980  United Kingdom .

*Primary Examiner*—Craig E. Church
*Attorney, Agent, or Firm*—Hill, Steadman & Simpson

[57] ABSTRACT

An x-ray computed tomography apparatus is operated so that a reconstruction of arbitrarily selectable volume regions can be accomplished. A Fourier reconstruction is implemented based on parallel data in planes that are inclined by the angle φ relative to a plane perpendicular to the z axis.

2 Claims, 5 Drawing Sheets

X-RAY COMPUTED TOMOGRAPHY APPARATUS

BACKGROUND OF THE INVENTION

1. Field of the Invention

The present invention is directed to an x-ray computed tomography apparatus of the type having an annular x-ray source surrounding a measuring field, the annular x-ray source having an annular anode that is scanned by an electron beam for generating a rotating x-ray beam. The geometry of such an x-ray computed tomography apparatus shall be referred to below as EBT (electron beam tomography) geometry.

2. Description of the Prior Art

An especially fast scanning of an examination subject is possible with an x-ray computed tomography apparatus of the above type, so that motion unsharpness is largely suppressed. In order for the x-ray beam to enter unimpeded into the measuring field wherein the examination subject lies, the radiation detector that is likewise annularly fashioned and is composed of a row of detector elements arranged laterally next to the exit window of the x-ray beam. This permits that the x-ray beam to emerge unimpeded from this window and to be incident on the x-ray detector after leaving the measuring field. To this end, the x-ray beam is inclined at an angle relative to its rotational axis that deviates slightly from 90°.

SUMMARY OF THE INVENTION

It is an object of the present invention to provide an x-ray computed tomography apparatus of the type generally described above wherein a fast, artifact-free image reconstruction is achieved.

The above object is achieved in accordance with the principles of the present invention in an x-ray computed tomography apparatus of the type generally described above which produces, for each scan, a set of measured values $f(u_i, p_k, \vartheta_l)$ for each scan for each projection angle $\vartheta_l$ and each position $u^i = z_i \cos \phi$ (wherein $\phi$ is the angle which the projection plane makes relative to the x-y plane of a Cartesian coordinate system) and each position $p_k$ in a selected direction from the z axis, and wherein, in accordance with the invention, an arbitrarily selectable excerpt of a volume image of the examination subject is obtained by two-dimensionally Fourier transforming the aforementioned data set with respect to $u_i$ and $p_k$ to obtain a frequency space function, multiplying the frequency space function by an interpolation function in one dimension of the frequency space and by a convolution core function in another dimension of the frequency space to obtain an interpolated, convoluted product, multiplying the interpolated, convoluted product by a phase factor which is dependent on a location of each point of the interpolated, convoluted product relative to a reconstruction volume in a locus space and thereby obtaining a file set of frequency space points, three-dimensionally gridding the final set of frequency space points onto points of a three-dimensional Cartesian grid with grid dimensions $\Delta\rho_x$, $\Delta\rho_y$ and $\Delta\rho_z$, freely selecting $\Delta\rho_x$, $\Delta\rho_y$ and $\Delta\rho_z$ to generate an arbitrarily selectable excerpt of the volume image, and by three-dimensionally fast Fourier transforming the arbitrary excerpt into the locus space. The excerpt transformed into the locus space is then displayed.

For generating an image in a plane x,y, which is arbitrarily oriented in space, the above-described apparatus can be modified so that no gridding takes place in the $\rho_z$ direction, and Fourier transformation is instead directly implemented for the position z=0. The gridding of the final set of frequency space points onto the Cartesian grid then takes place only on the basis of a two-dimensional gridding, with the dimensions $\Delta\rho_x$ and $\Delta\rho_y$ being freely selectable. The Fourier transformation into the locus space is then a two-dimensional fast Fourier transformation.

DESCRIPTION OF THE PREFERRED EMBODIMENTS

Figure 1:
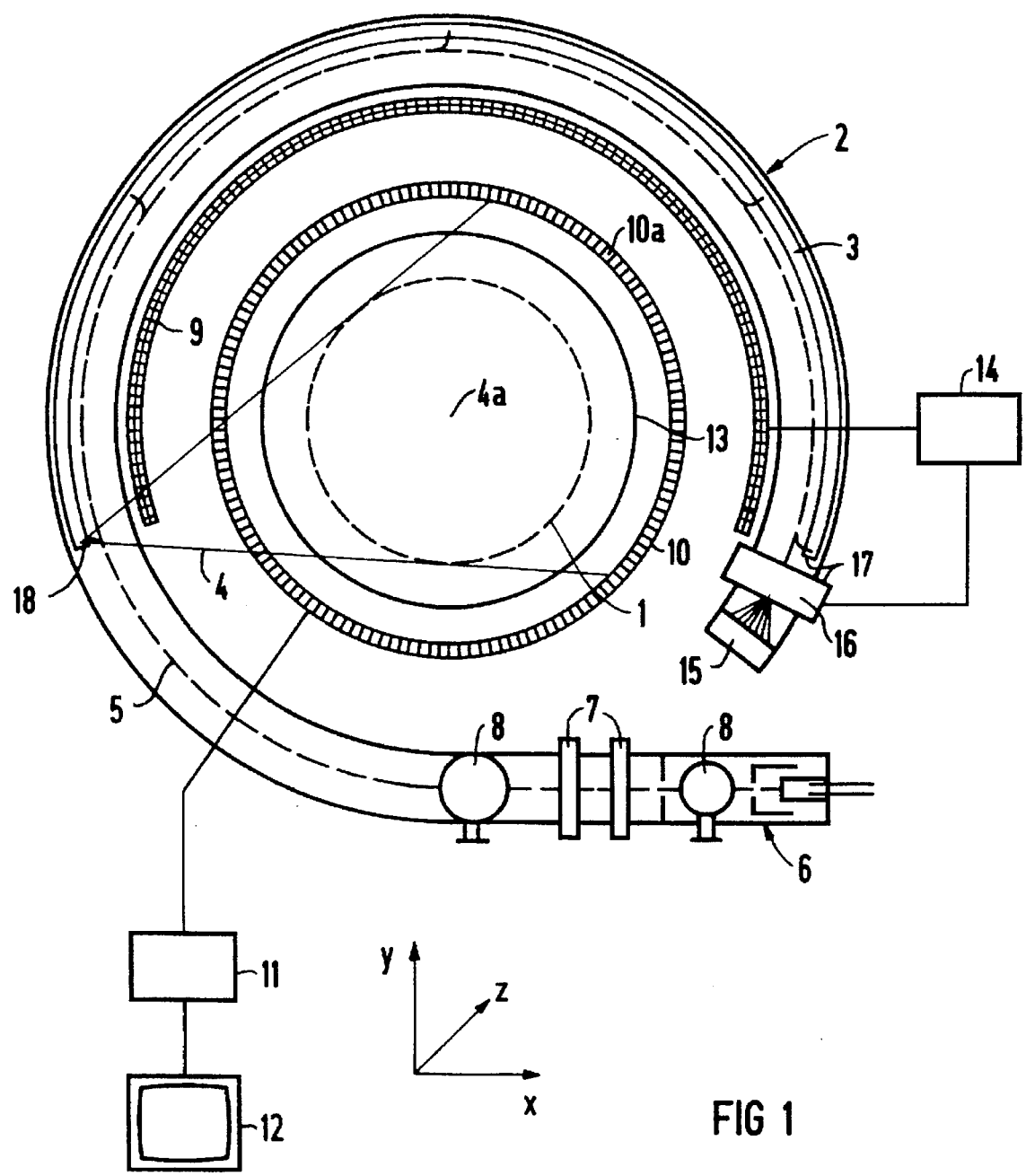
FIG. 1 is a schematic illustration of an x-ray computed tomography apparatus having EBT geometry for explaining the invention.

FIG. 1 shows an x-ray computed tomography apparatus having an annular x-ray source 2 surrounding a measuring field 1, a ring anode 3 being arranged in the x-ray source 2. The ring anode 3 is scanned by an electron beam 5 generated by an electron gun 6 for generating a rotating, fan-shaped x-ray beam 4. The electron gun 6 is followed by focusing coils 7. A vacuum in the x-ray source 2 is maintained by vacuum pumps 8. The electron beam 5 is deflected onto the ring anode 3 by a magnetic deflection coil 9 for generating the x-ray beam 4. The x-rays emerging after penetrating the examination subject in the measuring field 1 are acquired by an annular radiation detector 10 that is composed of a row of detector elements 10a. The output signals of the detector elements 10a are supplied to a computer 11 that calculates an image of the investigated slice of the examination subject therefrom and reproduces this image on a monitor 12. The measuring field 1 is a field in an opening 13 into which the examination subject is inserted. The x-ray beam 4 rotates on the ring anode 3 due to deflection of the electron beam 5 for irradiating the examination subject from different directions, rotating around the axis 4a.

A control unit 14 operates the deflection coil 9 such that the electron beam 5 penetrates the x-ray source 2 concentrically relative to the ring anode 3 before the beginning of a scan procedure until it reaches a radiation trap 15 of, for example, lead at the closed end. Before reaching the radiation trap 15, it is defocused by a defocusing means 16. For conducting a scan procedure, the electron beam 5 is deflected onto the ring anode 3 by the deflection coil 9 and scans the ring anode 3 from its end 17 to its end 18. Five focus positions are shown in FIG. 1. In fact, there are substantially more discrete focus positions, for example 1,000. Preferably, however, the focus should be continuously shifted by a traveling field, so that the scanning is determined by means of the detector interrogation (sampling). The x-ray beam 4 thus rotates opposite the direction of the electron beam 5 and is shown in its final position in FIG. 1. The scan procedure is ended at that point.

A renewed set-up of the annularly guided electron beam 5 subsequently ensues. A new scan procedure begins with the deflection thereof onto the end 17 of the ring anode 3.

It is also possible to scan the ring anode 3 with the electron beam 5 in the clockwise direction, i.e. from its end 18 to its end 17.

The radiation detector 10 is arranged such with respect to the ring anode 3 such that the x-ray beam 4 can pass by it before the x-ray beam 4 enters into the measuring field 1, and so that x-ray beam 4 is incident on the radiation detector 10 only after emerging from the measuring field 1.

In the exemplary embodiment, the ring anode 3 is fashioned as a partial ring, however, it can alternatively be fashioned as a full ring.

Geometry:

In EBT geometry, fan projections that are inclined by the angle φ relative to the x-y plane arise for discrete projection angles $\vartheta_l$ (φ is referred to as the "gyratory angle"). If the plane in which the fan at the angle $\vartheta_l$ lies has a vertical spacing $u_i$ from the coordinate origin, the intersection of this plane with the z axis is $z_i = u_i/\cos \phi$.

It will be assumed that a parallel projection in the same plane arises for each such fan projection as a result of re-interpolation, characterized by $\vartheta_l$, φ and $u_i$. This re-interpolation can be implemented substantially more simply than the interpolation of parallel data for φ=0 that initially seems desirable.

Figure 2:
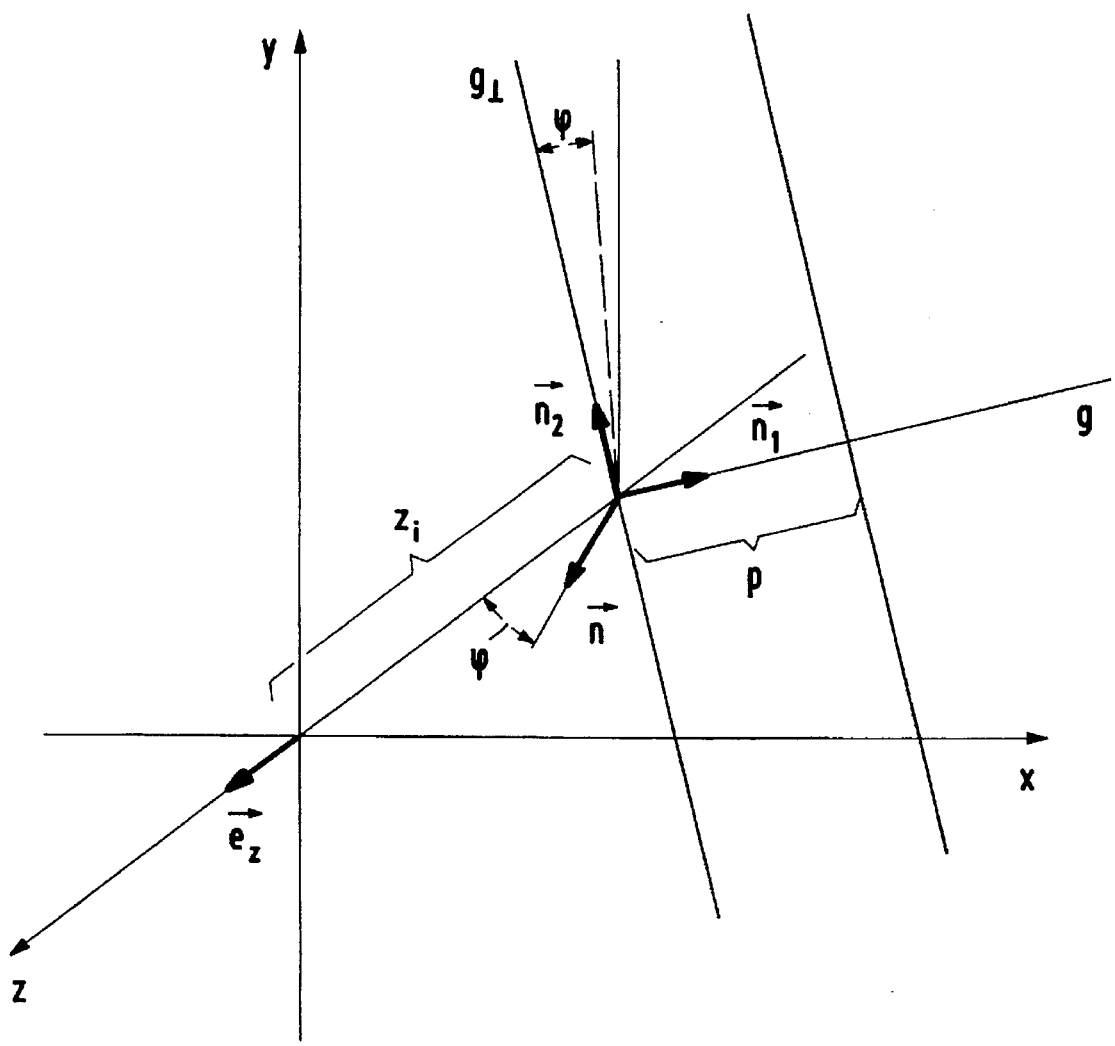
FIGS. 2–5 are geometrical illustrations for explaining the image reconstruction in the x-ray computed tomography apparatus of FIG. 1 in accordance with the principles of the present invention.
Figure 3:
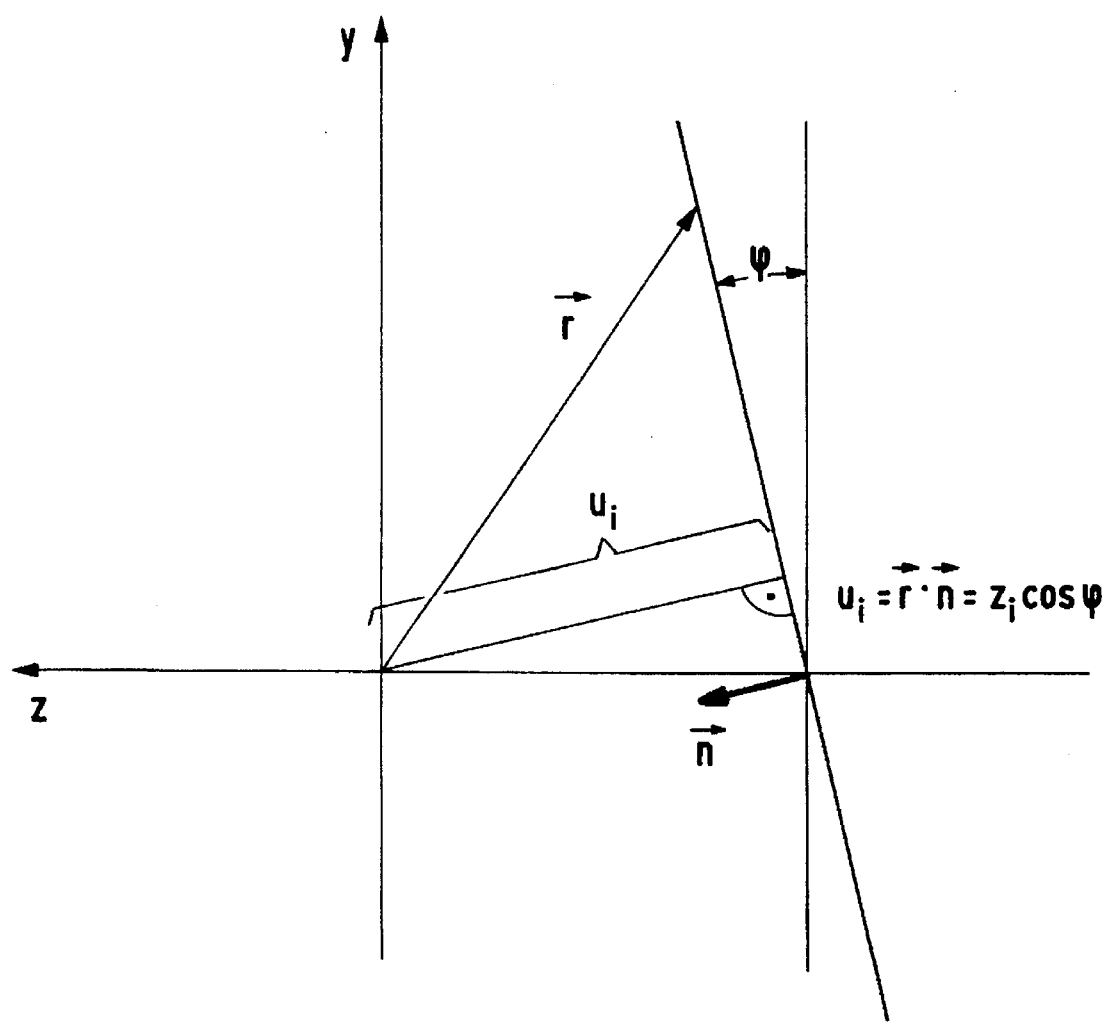

FIG. 2 and FIG. 3 illustrate the geometry, whereby FIG. 3 shows a view onto the y-z plane.

The straight line g ($\vec{n}_1$ direction) resides perpendicularly to the plane of the drawing, on the z axis. It proceeds through the point (0, 0, $z_i$) and describes the angle $\vartheta_l$ with the x-z plane.

The vector $\vec{r}_g$ for the line g is thus $$\vec{r}_g = z_i \vec{e}_z + p\vec{n}_1 \quad \text{with} \quad \vec{n}_1 = \begin{pmatrix} \cos \vartheta_l \\ \sin \vartheta_l \\ 0 \end{pmatrix} \quad (1)$$

The projection plane belonging to the angle $\vartheta_l$ is placed through g, this projection plane being inclined by the angle φ relative to the x-y plane. The projection plane contains the straight line g⊥, defined by the vector $$\vec{r}_{g\perp} = z_i \vec{e}_z + s\vec{n}_2 \quad \text{with} \quad \vec{n}_2 = \begin{pmatrix} -\sin \vartheta_l \cos\phi \\ \cos \vartheta_l \cos\phi \\ \sin\phi \end{pmatrix} \quad (2)$$

The vector $\vec{n}$ resides perpendicularly on the projection plane:

$$\vec{n} = \vec{n}_1 \times \vec{n}_2 = \begin{pmatrix} \sin \vartheta_l \sin\phi \\ -\cos \vartheta_l \sin\phi \\ \cos\phi \end{pmatrix} \quad (3)$$

The vectors $\vec{n}_1$, $\vec{n}_2$ and $\vec{n}$ define an orthogonal coordinate system.

It is expedient to characterize an attenuation value lying in the projection plane established by $\vartheta_l$ and $u_i$ in the following way:

1) By the distance $u_i$ of the projection plane from the coordinate origin:

$$u_i = \vec{r}_i \cdot \vec{n} = z_i \cos\phi$$

2) By the "projection angle" $\vartheta_l$

3) By the distance $p_k$ of the measured value in $\vec{n}_1$ direction from the z axis.

One thus has a set of measured values $f(u_i, p_k, \vartheta_l)$.

The scan grid in the $\vec{n}_1$ direction is a; the scan grid in the $\vec{n}$ direction is $a_\perp$; $N_p$ projections are registered per "revolution":

$$p_k = (k - 0.5 + a_m)a \quad k = \ldots -1,0,1 \ldots \quad (4)$$
$$u_i = ia_\perp + du(\vartheta_l) \quad i = \ldots -1,0,1, \ldots$$
$$\vartheta_l = \frac{(l-1)\pi}{N_P} \quad l = 1, 2, \ldots, N_P$$

wherein $a_m$ is the alignment.

The term $du(\vartheta_l)$ takes into consideration that the data are acquired as "spiral data". During the exposure, the measured subject moves with a constant feed rate in the z direction relative to the rotating x-ray beam 4, so that the position in the $\vec{n}$ direction has changed by exactly $a_\perp$ after one revolution ($N_p$ projections) (and changed by $a_\perp/\cos \phi$ in the z direction).

The operating mode wherein the measured subject is stationary during a complete revolution and is shifted by $a_\perp/\cos \phi$ in the z direction after every revolution is representable as a special case for $du(\vartheta_l)=0$.

Possible definitions of a three-dimensional reference image for the Fourier reconstruction:

When a three-dimensional image $B_0(\vec{r})$ is to be constructed from the line integrals $f(u_i, p_k, \vartheta_l)$, in order for this three-dimensional image to correctly quantitatively reproduce the subject attenuation values $\mu(\vec{r})$, the integrals $f(u_i, p_k, \vartheta_l)$ must linearly contribute to $B_0(\vec{r})$:

$$B_0(\vec{r}) = \sum_l \sum_i \sum_k G_{lik}(\vec{r}) f(u_i, p_k, \vartheta_l) \quad (5)$$

$G_{lik}(\vec{r})$ must be the same for all $\vec{r}$ on straight lines parallel to the projection line $(u_i, p_k, \vartheta_l)$, i.e. in the $\vec{n}_2$ direction and can therefore be dependent only on the distance of the point $\vec{r}$ from proportion line $(u_i, p_k, \vartheta_l)$. This distance can in turn be divided into the distance in the $\vec{n}$ direction $d_\perp = \vec{r} \cdot \vec{n} - u_i$ of the point $\vec{r}$ from the projection plane characterized by $u_i$ and $\vartheta_l$ and into the distance $d = \vec{r} \cdot \vec{n}_1 - p_k$ between the projection of the point into the projection plane and the projection line.

Because the inclination angle φ in EBT geometry is small and because the conventional spiral scan must be contained in the representation as a special case for φ=0, the distance dependency is described by the product of two functions, each of which is respectively dependent on one of the two distance components:

$$G_{lik}(\vec{r}) = L_{lik}(\vec{r} \cdot \vec{n}_1 - p_k) h_{lik}(\vec{r} \cdot \vec{n} - u_i) \quad (6)$$

when all projection values $f(u_i, P_k, \vartheta_l)$ are identically treated.

$$B_0(\vec{r}) = \frac{2a_\perp}{\pi a N_P} \sum_l \sum_i \sum_k f(u_i, p_k, \vartheta_l) L_0(\vec{r} \cdot \vec{n}_1 - p_k) h(\vec{r} \cdot \vec{n} - u_i) \quad (7)$$

arises according to a standard scaling.

This image is considered as "reference image" for the Fourier reconstruction. The goal of a Fourier reconstruction method must be to reproduce $B_0(\vec{r})$ in the image region under consideration.

In a conventional spiral scan (φ=0), h(u) is the interpolation function in the z direction. $L_0(p)$ is the normal convolution core whose Fourier transform $\hat{L}_0(\rho)$ is related to the modulation transfer function $M_A(\rho)$ of the reconstruction in the following way:

$$\hat{L}_0(\rho) = \frac{\pi^2 a^2}{2} |\rho| M_A(\rho) \quad \text{spiral scan} \tag{8}$$

In the general case ($\phi \neq 0$), $$\hat{L}_0(\rho) = \frac{\pi^2 a^2}{2} |\rho| M_A(\rho) \cos\phi \tag{9}$$

is valid for $\hat{L}_0(\rho)$.

Derivation of a three-dimensional Fourier reconstruction method: reconstruction of the entire measurement volume:

Theoretical Description

Let the diameter of the measuring field in the x direction and in the y direction be $D_M$. Let the expanse (thickness) of the measuring field in the z direction be $D_z$.

When $$L(p) = L_0(p) \text{ for } |p| \leq D_M$$

$$L(p) = 0 \text{ for } |p| > D_M \tag{10}$$

is set (exactly as in the two-dimensional case), the projections in the $\vec{n}_1$ direction convoluted with $L(p)$ can be periodically continued without degrading the image in the measuring field region, when $$w \leq 2D_M$$

is valid for the period length w. The function h(u) will be of slight expanse in the locus space anyway (expanse on the order of magnitude of a slice width b; in the case of the spiral scan, h(u), for example, is the linear interpolation between neighboring slices).

$$v \leq D_z + b$$

The image $B_1(\vec{r})$ defined in the following way is identical to $B_0(\vec{r})$ in the measuring field region:

$$B_1(\vec{r}) = \tag{11}$$

$$\frac{2a_\perp}{\pi a N_P} \sum_m \sum_n \sum_l \sum_i \sum_k f(u_i, p_k, \vartheta_l) L(\vec{r}\cdot\vec{n}_1 - p_k - mw) h(\vec{r}\cdot\vec{n} - u_i - nv)$$

The three-dimensional Fourier transform $\hat{B}_1(\vec{\rho})$ of this image reads:

$$\hat{B}_1(\vec{\rho}) = \frac{2a_\perp}{\pi a N_P} \sum_m \sum_n \sum_l \sum_i \sum_k \times \tag{12}$$

$$\times \iiint d(\vec{r}\cdot\vec{n}) d(\vec{r}\cdot\vec{n}_1) d(\vec{r}\cdot\vec{n}_2) \times$$

$$\times f(u_i, p_k, \vartheta_l) L(\vec{r}\cdot\vec{n}_1 - p_k - mw) h(\vec{r}\cdot\vec{n} - u_i - nv) \times$$

$$\times \exp(-2\pi i (\vec{\rho}\cdot\vec{n})(\vec{r}\cdot\vec{n})) \exp(-2\pi i \cdot$$

$$\vec{n}_1)(\vec{r}\cdot\vec{n}_1)) \exp(-2\pi i (\vec{\rho}\cdot\vec{n}_2)(\vec{r}\cdot\vec{n}_2))$$

The integral over $(\vec{r}\cdot\vec{n}_2)$ is a $\delta$ function and is derived as:

$$\int d(\vec{r}\cdot\vec{n}_2) \exp(-2\pi i (\vec{\rho}\cdot\vec{n}_2)(\vec{r}\cdot\vec{n}_2)) = \delta(\vec{\rho}\cdot\vec{n}_2) \tag{13}$$

Also valid is:

$$\sum_m \int d(\vec{r}\cdot\vec{n}_1) L(\vec{r}\cdot\vec{n}_1 - p_k - mw) \exp(-2\pi i (\vec{\rho}\cdot\vec{n}_1)(\vec{r}\cdot\vec{n}_1)) = \tag{14}$$

$$\sum_m \hat{L}(\vec{\rho}\cdot\vec{n}_1) \exp(-2\pi i (\vec{\rho}\cdot\vec{n}_1) p_k) \exp(-2\pi i (\vec{\rho}\cdot\vec{n}_1) mw)$$

When $\rho = \vec{\rho}\cdot\vec{n}_1$ is set, then, because $$\sum_m \exp(-2\pi i \rho m w) = \Delta\rho \sum_m \delta(\rho - m\Delta\rho), \text{ with } \Delta\rho = 1/w \tag{15}$$

the following is valid:

$$\sum_m \int d(\vec{r}\cdot\vec{n}_1) L(\vec{r}\cdot\vec{n}_1 - p_k - mw) \exp(-2\pi i (\vec{\rho}\cdot\vec{n}_1)(\vec{r}\cdot\vec{n}_1)) = \tag{16}$$

$$\Delta\rho \sum_m \hat{L}(m\Delta\rho) \exp(-2\pi i m \Delta\rho p_k) \delta(\rho - m\Delta\rho)$$

In the same way, one obtains $$\sum_n \int d(\vec{r}\cdot\vec{n}) h(\vec{r}\cdot\vec{n} - u_i - nv) \exp(-2\pi i (\vec{\rho}\cdot\vec{n})(\vec{r}\cdot\vec{n})) = \tag{17}$$

$$\Delta\rho_\perp \sum_n \hat{h}(n\Delta\rho_\perp) \exp(-2\pi i n \Delta\rho_\perp u_i) \delta(\rho_\perp - n\Delta\rho_\perp)$$

with $\Delta\rho_\perp = \vec{\rho}\cdot\vec{n}$ and $\Delta\rho_\perp = 1/v$.

Equations (13), (16) and (17) introduced into (12) leads to the result:

$$\hat{B}_1(\vec{\rho}) = \frac{2a_\perp \Delta\rho \Delta\rho_\perp}{\pi a N_P} \sum_l \delta(\vec{\rho}\cdot\vec{n}_2) \times \tag{18}$$

$$\sum_m \sum_n \hat{f}(n\Delta\rho_\perp, m\Delta\rho, \vartheta_l) \hat{L}(m\Delta\rho) \hat{h}(n\Delta\rho_\perp) \times$$

$$\times \delta(\rho - m\Delta\rho) \delta(\rho_\perp - n\Delta\rho_\perp)$$

with $\rho = \vec{\rho}\cdot\vec{n}_1$ and $\rho_\perp = \vec{\rho}\cdot\vec{n}$.

$\hat{f}(n\Delta\rho_\perp, m\Delta\rho, \vartheta_l)$ is the two-dimensional, discrete Fourier transform of $f(u_i, p_k, \vartheta_l)$ with respect to $u_i$ and $p_k$:

$$\hat{f}(n\Delta\rho_\perp, m\Delta\rho, \vartheta_l) = \sum_i \sum_k f(u_i, p_k, \vartheta_l) \exp(-2\pi i m \Delta\rho p_k) \exp(-2\pi i n \Delta\rho_\perp u_i) \tag{19}$$

$$\sum_i \sum_k f(i, k, \vartheta_l) \exp(-2\pi i m \Delta\rho k a) \exp(-2\pi i n \Delta\rho_\perp i a_\perp) \times$$

$$\times \underbrace{\exp(-2\pi i m \Delta\rho (0.5 - a_m) a) \exp(2\pi i n \Delta\rho_\perp du(\vartheta_l))}_{\text{phase factor}}$$

whereby Equation (4) was employed.

Equation (18) means that a continuous, three-dimensional image $B_1(\vec{r})$ was defined in the locus space whose three-dimensional Fourier transform $\hat{B}_1(\vec{\rho})$ in the frequency space exists only at discrete points. Therebetween, $\hat{B}_1(\vec{\rho})$ has no values.

Values on a plane $\vec{\rho}\cdot\vec{n}_2 = 0$ in the frequency space belong to each "projection angle" $\vartheta_l$. This plane is inclined relative to the $\rho_x$–$\rho_z$ plane by the "projection angle" $\vartheta_l$ and by the "gyroscopic angle" $\phi$.

This is a generalization of a theorem referred to as the "central slice theorem" in two-dimensions. In the present context, it can be stated as follows:

The three-dimensional Fourier transform $\overset{\wedge\wedge}{B}_1(\vec{\rho})$ of the image $B_1(\vec{r})$ on a plane in the frequency space that proceeds through the origin and is inclined relative to the $\rho_x$-$\rho_z$ plane by the "projection angle" $\vartheta_l$ and by the "gyroscopic angle" $\phi$ is equal to the two-dimensional Fourier transform of the projections $\hat{f}(n\Delta\rho_\perp, m\Delta\rho, \vartheta_l) \hat{L}(m\Delta\rho) \hat{h}(n\Delta\rho_\perp)$ registered for each angle $\vartheta_l$.

The values of the plane defined by and associated with the "projection angle" $\vartheta_l$ are present in a Cartesian, discrete grid, having the grid dimension $\Delta\rho$ in the $\vec{n}_1$ direction and $\Delta\rho_\perp$ in the $\vec{n}$ direction.

In order to create the basis for a three-dimensional Fourier back-transformation of the spectrum into the locus space with FFT algorithms, a new image $B_2(\vec{r})$ is defined, this arising from $B_1(\vec{r})$ by multiplication with the step function $T(\vec{r})$:

$$T(\vec{r})=T_1(x)T_1(y)T_2(z)$$

$$T_1(x)=1 \text{ for } |x|\leq D_B/2$$

$$T_1(x)=0 \text{ for } |x|>D_B/2$$

$$T_2(z)=1 \text{ for } |z|\leq D_Z/2$$

$$T_2(z)=0 \text{ for } |z|>D_Z/2 \quad (20)$$

$D_B \cdot D_B$ is the central image excerpt of interest in the x-y plane, $D_Z$ is the length of the measuring field in z direction. The image $B_2(\vec{r})$ coincides with $B_1(\vec{r})$ in volume $D_B \cdot D_B \cdot D_Z$; outside of this volume, it is zero. The periodic repetition of the image in the locus space occurring due to the spectrum scanning in the Cartesian coordinates given the three-dimensional FFT therefore does not lead to overlap errors.

$$B_2(\vec{r})=B_1(\vec{r})T_1(x), T_1(y), T_2(z) \quad (21)$$

is set.

The following are then valid:

$$\overset{\wedge\wedge}{B}_2(\rho_x,\rho_y,\rho_z) = \iiint dx\,dy\,dz\, \exp(-2\pi i\rho_x x)\exp(-2\pi i\rho_y y)\exp(-2\pi i\rho_z z) \times \quad (22)$$

$$\times \frac{2a_\perp}{\pi a N_P} \sum_l \sum_i \sum_k \sum_m \sum_n f(u_i,p_k,\vartheta_l)L(\vec{r}\cdot \vec{n}_1 - p_k - mw)h(\vec{r}\cdot\vec{n} - u_i - nv) \times$$

$$\times T_1(x)T_1(y)T_2(z)$$

$$\vec{r}\cdot\vec{n}_1 = x\cos\vartheta_1 + y\sin\vartheta_1 \quad (23)$$

$$\vec{r}\cdot\vec{n} = x\sin\vartheta_1\sin\phi - y\cos\vartheta_1\sin\phi + z\cos\phi \quad (24)$$

With $\rho=\vec{\rho}\cdot\vec{n}_1$, one can thus write:

$$\sum_m L(\vec{r}\cdot\vec{n}_1 - p_k - mw) = \sum_m L(x\cos\vartheta_l + y\sin\vartheta_l - p_k - mw) = \quad (25)$$

$$\sum_m \int d\rho L(\rho)\exp(2\pi i\rho(x\cos\vartheta_l + y\sin\vartheta_l - p_k - mw)) =$$

$$\Delta\rho \sum_m \hat{L}(m\Delta\rho)\exp(-2\pi i m\Delta\rho p_k)\exp(2\pi i m\Delta\rho x\cos\vartheta_l)\exp(2\pi i m\Delta\rho y\sin\vartheta_l)$$

The equality $$\sum_m \exp(-2\pi i\rho mw) = \Delta\rho \sum_m \delta(\rho - m\Delta\rho), \text{ with } \Delta\rho = 1/w \quad (26)$$

was thereby used (also see (15)).

With $\rho_\perp=\vec{\rho}\cdot\vec{n}$, one likewise obtains:

$$\sum_n h(\vec{r}\cdot\vec{n} - u_i - nv) = \quad (27)$$

$$\sum_n h(x\sin\vartheta_l\sin\phi - y\cos\vartheta_l\sin\phi + z\cos\phi - u_i - uv) =$$

$$\sum_n \int d\rho_\perp \hat{h}(\rho_\perp)\exp(2\pi i\rho_\perp(x\sin\vartheta_l\sin\phi - y\cos\vartheta_l\sin\phi + z\cos\phi - u_i - nv))$$

$$\Delta\rho_\perp \sum_n \hat{h}(n\Delta\rho_\perp)\exp(-2\pi i n\Delta\rho_\perp u_i) \times$$

$$\times \exp(2\pi i n\Delta\rho_\perp x\sin\vartheta_l\sin\phi)\exp(-2\pi i n\Delta\rho_\perp y\cos\vartheta_l\sin\phi)\exp(2\pi i n\Delta\rho_\perp z\cos\phi)$$

Equations (25) and (27) introduced into (22) results in:

$$\overset{\wedge\wedge}{B}_2(\rho_x,\rho_y,\rho_z) = \quad (28)$$

$$\frac{2a_\perp\Delta\rho\Delta\rho_\perp}{\pi a N_P} \sum_l \sum_m \sum_n \sum_i \sum_k \underbrace{f(u_i,p_k,\vartheta_l)\exp(-2\pi i m\Delta\rho p_k)\exp(-2\pi i n\Delta\rho_\perp u_i)}_{\hat{f}(n\Delta\rho_\perp, m\Delta\rho, \vartheta_l)} \times$$

$$\times \hat{L}(m\Delta\rho)\hat{h}(n\Delta\rho_\perp) \times$$

$$\times \int dx\, T_1(x)\exp(-2\pi i x(\rho_x - m\Delta\rho\cos\vartheta_1 - n\Delta\rho_\perp\sin\vartheta_1\sin\phi)) \times$$

$$\times \int dy\, T_1(y)\exp(-2\pi i y(\rho_y - m\Delta\rho\sin\vartheta_1 + n\Delta\rho_\perp\cos\vartheta_1\sin\phi)) \times$$

$$\times \int dz\, T_2(z)\exp(-2\pi i z(\rho_z - n\Delta\rho_\perp\cos\phi)) =$$

$$= \frac{2a_\perp\Delta\rho\Delta\rho_\perp}{\pi a N_P} \sum_l \sum_m \sum_n \hat{f}(n\Delta\rho_\perp, m\Delta\rho, \vartheta_l)\hat{L}(m\Delta\rho)\hat{h}(n\Delta\rho_\perp) \times$$

$$\times \hat{T}_1(\rho_x - m\Delta\rho\cos\vartheta_1 - n\Delta\rho_\perp\sin\vartheta_1\sin\phi) \times$$

$$\times \hat{T}_1(\rho_y - m\Delta\rho\sin\vartheta_1 + n\Delta\rho_\perp\cos\vartheta_1\sin\phi) \times$$

$$\times \hat{T}_2(\rho_z - n\Delta\rho_\perp\cos\phi)$$

$\overset{\wedge\wedge}{B}_1(\vec{\rho})$, the three-dimensional Fourier transform of the image $B_1(\vec{r})$ unlimited in the locus space, is only defined at discrete points in the frequency space (see equation (18)).

$\overset{\wedge\wedge}{B}_2(\vec{\rho})$, by contrast, the three-dimensional Fourier transform of the image $B_1(\vec{r})$ multiplied by the step function $T_1(x)\,T_1(y)\,T_2(z)$ has continuous values in the frequency space. $\overset{\wedge\wedge}{B}_2(\vec{\rho})$ arises by convolution of the discrete $\overset{\wedge\wedge}{B}_1(\vec{\rho})$ with the one-dimensional Fourier transform $\hat{T}_1(\rho_x)\, \hat{T}_1(\rho_y)\, \hat{T}_2(\rho_z)$ of $T_1(x)\,T_1(y)\,T_2(z)$.

$\overset{\wedge\wedge}{B}_2(\vec{\rho})$ is obtained at the location $(\rho_x, \rho_y, \rho_z)$ by calculating the distance of the point $(\rho_x, \rho_y, \rho_z)$ from every point $(n\Delta\rho_\perp, m\Delta\rho, \vartheta_l)$ of $\overset{\wedge\wedge}{B}_1(\vec{\rho})$ in the $\rho_x$ direction (i.e., $\rho_1=\rho_x-m\Delta\rho\cos\vartheta_l-n\Delta\rho_\perp\sin\vartheta_l\sin\phi$) in the $\rho_y$ direction (i.e., $\rho_2=\rho_y-m\Delta\rho\sin\vartheta_l+n\Delta\rho_\perp\cos\vartheta_l\sin\phi$), and in $\rho_z$ direction (i.e., $\rho_3=\rho_z-n\Delta\rho_\perp \cos\phi$), the value of the point ($n\Delta\rho_\perp$, $m\Delta\rho$, $\phi_l$) is weighted with $\hat{T}_1(\rho_1)\,\hat{T}_1(\rho_2)\hat{T}_2(\rho_3)$ and all such contributions are added.

The continuous spectrum $\overset{\wedge}{B}_1(\vec{\rho})$ can then be scanned in the raster points $\alpha\Delta\rho_x$, $\beta\Delta\rho_y$, $\gamma\Delta\rho_z$ with $$\Delta\rho_x \leq 1/D_B$$

$$\Delta\rho_y \leq 1/D_B$$

$$\Delta\rho_z \leq 1/D_Z$$

which are transformed into the locus space with a three-dimensional FFT without aliasing errors occurring in the periodic repetition of the image $B_2(\vec{r})$ following therefrom.

As in the two-dimensional case, the method can be simply expanded to arbitrary, non-central image excerpts $D_B \cdot D_B$ in the x-y plane, as follows. Let the desired reconstruction center lie at the location $$\vec{r}_z = (r_z\cos\vartheta_z, r_z\sin\vartheta_z, Z_z) \tag{29}$$

A shift of the reconstruction center in the z direction is possible but not actually meaningful because one could then just position the patient differently, or shorten the length of the scan region, in order to keep the radiation stress as low as possible.

After the ideational shift of the image $B_1(\vec{r})$ by the vector $-\vec{r}_z$, so that the reconstruction center again comes to lie on the coordinate origin, one multiplies with the step function $T_1(x)\,T_1(y)\,T_2(z)$ in order to obtain $B_2(\vec{r})$. Shift by $-\vec{r}_z$ in the frequency space means multiplication with a phase factor.

With $$\vec{r}_z \cdot \vec{n} = r_z(\cos\vartheta_z\cos\vartheta_l+\sin\vartheta_z\sin\vartheta_l)=r_z\cos(\vartheta_l-\vartheta_z) \tag{30}$$

$$\vec{r}_z \cdot \vec{n} = r_z(\cos\vartheta_z\sin\vartheta_l\sin\phi-\sin\vartheta_z\cos\vartheta_l\sin\phi)+z_z\cos\phi=r_z\sin\phi\sin(\vartheta_l-\vartheta_z)+z_z\cos\phi \tag{31}$$

one obtains the following for three-dimensional Fourier reconstruction from EBT data:

$$B_{z,2}(\vec{r}) = B_1(\vec{r}-\vec{r}_z)T_1(x)T_1(y)T_2(z) \tag{32}$$

$$\tag{33}$$

$$\overset{\wedge}{B}_{z,2}(\rho_x,\rho_y,\rho_z) = \iiint dx\,dy\,dx\exp(-2\pi i\rho_x x)\exp(-2\pi i\rho_y y)\exp(-2\pi i\rho_z z) \times$$

$$\times \frac{2a_\perp}{\pi a N_P} \sum_l \sum_i \sum_k \sum_m \sum_n f(u_i,p_k,\vartheta_l) \times$$

$$\times L((\vec{r}-\vec{r}_z)\cdot\vec{n}_1-p_k-mw)h((\vec{r}-\vec{r}_z)\cdot\vec{n}-u_i-nv) \times$$

$$\times T_1(x)T_1(y)T_2(z) =$$

$$\frac{2a_\perp\Delta\rho\Delta\rho_\perp}{\pi a N_P}\sum_l\sum_m\sum_n \hat{f}(n\Delta\rho_\perp,m\Delta\rho,\vartheta_l)\hat{L}(m\Delta\rho)\hat{h}(n\Delta\rho_\perp) \times$$

$$\times \underbrace{\exp(-2\pi i m\Delta\rho_\perp r_z\cos(\vartheta_l-\vartheta_z))}_{\text{phase factor}} \times$$

$$\times \underbrace{\exp(-2\pi i n\Delta\rho_\perp r_z\sin\phi\sin(\vartheta_l-\vartheta_z)+z_z\cos\phi))}_{\text{phase factor}} \times$$

$\times \hat{T}_1(\rho_x - m\Delta\rho\cos\vartheta_1 - n\Delta\rho_\perp\sin\vartheta_1\sin\phi) \times$ $\times \hat{T}_1(\rho_y - m\Delta\rho\sin\vartheta_1 + n\Delta\rho_\perp\cos\vartheta_1\sin\phi) \times$ $\times \hat{T}_2(\rho_z - n\Delta\rho_\perp\cos\phi)$ An arbitrary rotation of the illustrated image volume around the point ($r_z\cos\vartheta_z$, $r_z\sin\vartheta_z$, $Z_z$) can also be realized without significant additional outlay, so that reformattings can be thereby replaced up to a certain degree.

Simplifications for the practical realization:

As in the two-dimensional case, of course, the image $B_1(\vec{r})$ in the locus space will not be limited with an ideal rectangular stop since the Fourier transform thereof is $$\hat{T}_1(\rho_x)\hat{T}_1(\rho_y)\hat{T}_2(\rho_z) = D_B^2 D_Z\,\text{sinc}(\pi\rho_x D_B)\text{sinc}(\pi\rho_y D_B)\text{sinc}(\pi\rho_z D_z) \tag{34}$$

so that every point of $\overset{\wedge}{B}_1(\vec{\rho})$ contributes to every point of $\overset{\wedge}{B}_2(\vec{\rho})$ ($\alpha\Delta\rho_x$, $\beta\Delta\rho_y$, $\gamma\Delta\rho_z$). Instead, a volume $D_R\cdot D_R\cdot D_Z$ is reconstructed that is larger than the desired image volume $D_B\cdot D_B\cdot D_Z$, and step functions $T_1$ and $T_2$ are selected such that $T_1$ decreases or fades to an adequate extent along the path from $D_B/2$ to $D_R-D_B/2$ and $T_2$ decreases or fades to an adequate extent along the path from $D_Z/2$ to $D_Z-D_Z/2$ and subsequently no longer upwardly exceeds a smallest value $\epsilon_{min}$. Suitable functions, for example, are the modified Van der Maas window, the Blackman window or a combination of the two.

In the spiral mode, the data in the z direction arise in a dense sequence for an EBT apparatus, i.e. the grid $a_\perp$ is extremely small. When, for example, one sets a 3 mm slice and a patient feed of 3 mm per second is undertaken in z the direction, a revolution will last approximately 50 ms, with 20 revolutions per second, and thus, $$a_\perp = \frac{3\text{ mm}}{20}\cos(0.5\pi/180) = 0.15\text{ mm}$$

given a gyroscopic angle of 0.5°.

Approximately 400 slices are obtained in the z direction for $D_z=60$ mm, so that the two-dimensional Fourier transformation of the projections $f(u_i, p_k, \vartheta_l)$ in the $\vec{n}_1$ direction ($p_k$) would, as before, have to be of the dimension 2048 or 4096 dependent on the number of detector elements, also of the dimension 512 in the direction $\vec{n}(u_i)$ (impractically large).

Since the slice thickness b (for example 3 mm), however, is significantly larger than the spacing of neighboring slices ($a_\perp=0.15$ mm), a number of projections that have arisen given the same projection angle $\vartheta_l$ and follow one another in the $\vec{n}$ direction ($u_i$ with ascending index i) can be combined, so that an effective $a_\perp$ of approximately half the slice thickness b arises and thus only 64 supporting points, for example, for the Fourier transmission of the projection $f(u_i, p_k, \vartheta_l)$ in the $\vec{n}$ direction.

The unsharpening of the image in z direction that is unavoidable in this combination can be compensated by including a steepening part in $\hat{h}(n\Delta\rho_\perp)$.

Quasi-two-Dimensional Fourier Reconstruction of Individual Slices:

The three-dimensional Fourier reconstruction of the entire measurement volume makes high demands of storage space and calculating speed.

In the example that has been mentioned (3 mm slice, length of the measurement field in the z direction $D_z=60$ mm), the projections $f(u_i, p_k, \vartheta_l)$ must first be transformed with two-dimensional FFTs of the length 2048·64 into the frequency space for every projection angle $\vartheta_l$ (given 1024 detector elements). When, for example, 1000 projections arise per revolution, 1000 of these two-dimensional FFTs then must be implemented. The multiplication by $\hat{L}(m\Delta\rho)$ and $\hat{h}(n\Delta\rho_\perp)$ as well as by the phase factor subsequently ensues in the frequency space. $\hat{B}_{z,1}(\vec{\rho})$ is thus defined. When a two-dimensional image having a 512·512 matrix is presented and when one wishes the images in approximately the spacing of half the slice thickness, i.e. approximately 40–50 images for $D_z=60$ mm, then—due to the properties of the step function $T_1(x)$ $T_1(y)$ $T_2(z)$—the three-dimensional Fourier back-transformation into the locus space must be of the dimension 1024·1024·128, i.e. $\hat{B}_{z,2}(\rho_x, \rho_y, \rho_z)$ is required at just as many supporting points. When $T_1$ and $T_2$ are suitably selected, $\hat{B}_{z,1}(\vec{\rho})$ contributes to approximately 4·4·4 points of $\hat{B}_{z,1}(\rho_x, \rho_y, \rho_z)$.

It is also a disadvantage that one cannot begin with the reconstruction until all data have been registered, i.e. until after the entire scan.

For these reasons, it may be desirable to reconstruct successive two-dimensional images as before (for instance, in the spacing of half a slice thickness). Only a relatively small data set is then required for the reconstruction of the first image.

A quasi-two-dimensional Fourier construction method for EBT data shall be set forth below.

Figure 4:
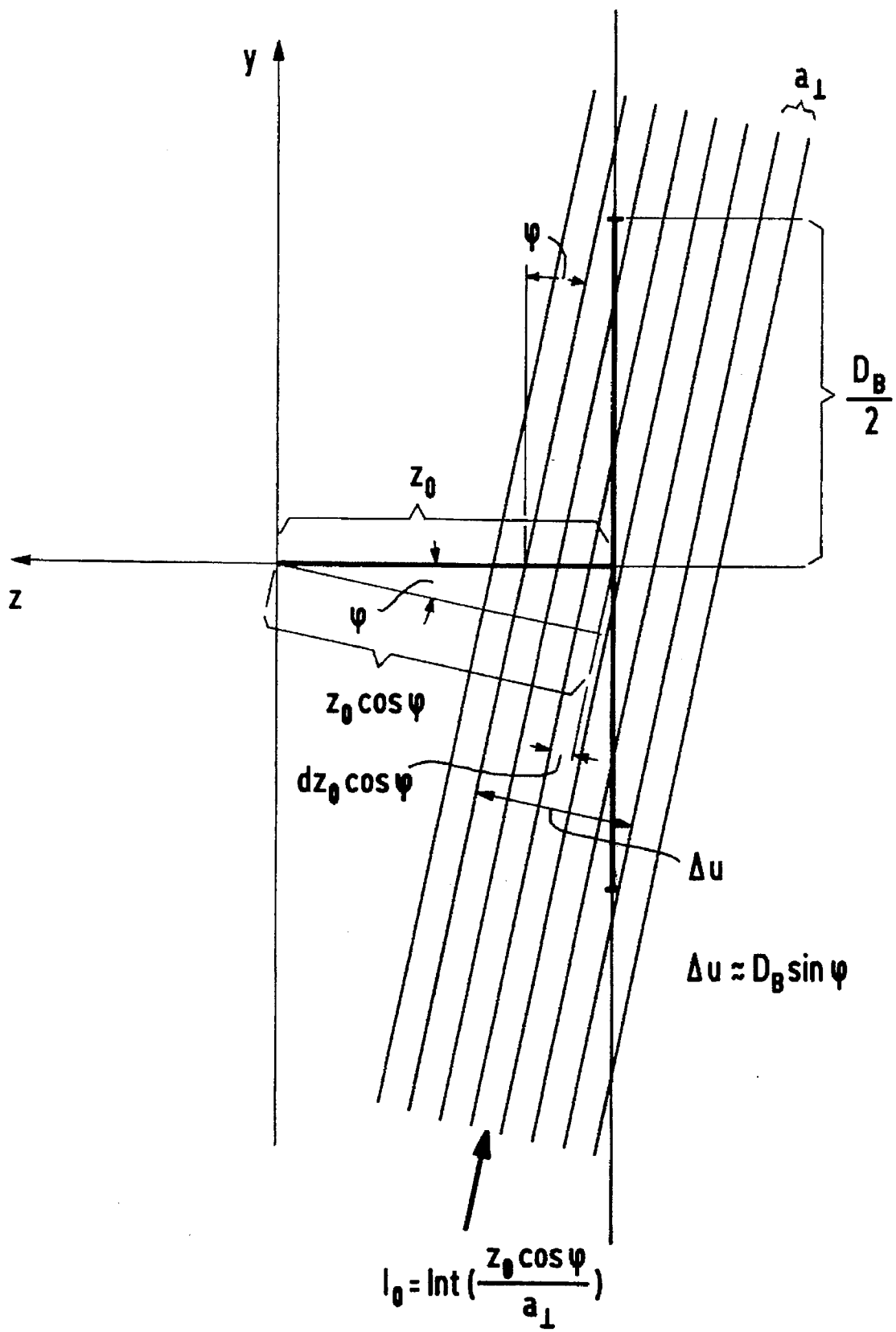

Is seen in the y-z plane, FIG. 4 shows the desired slice at $z_0$ as well as the region $\Delta u$ in the $\vec{n}$ direction from which data contribute to the image at $z_0$. When $$l_0 = \text{Int}\left(\frac{z_0\cos\phi}{a_\perp}\right) \qquad (35)$$

$$l = \text{Int}\left(\frac{\Delta u}{2a_\perp}\right) + 1$$

is introduced, then $u_i$ must be taken into consideration for $$l_0 - l \leq i \leq l_0 + l \qquad (36)$$

Analogous to equation (11), an image $B_{1,l_0}(\vec{r})$ is now defined—although two-dimensionally—at the location $\vec{r} = (x, y, z_0)$, whereby the projections $f(u_i, p_k, \vartheta_l)$ in the $\vec{n}_\perp$ direction convoluted with $L(p)$ and $h(u)$ are repeated as in (11) with period $w=2D_M$, but with the period $v'=\Delta u+B$ in the $\vec{n}$ direction (b is the expanse of $h(u)$):

$$B_{1,l_0}(\vec{r}) = \frac{2a_\perp}{\pi a N_p} \sum_m \sum_n \sum_{l=l_0-l}^{l_0+l} \sum_k f(u_i, p_k, \vartheta_l) L(\vec{r} \cdot \vec{n}_\perp - p_k - mw) h(\vec{r} \cdot \vec{n} - u_i - nv') \qquad (37)$$

with $\vec{r} = (x, y, z_0)$

Because $$\vec{r} \cdot \vec{n}_\perp = x\cos\vartheta_l + y\sin\vartheta_l \qquad (38)$$

$$\vec{r} \cdot \vec{n} = x\sin\vartheta_l\sin\phi - y\cos\vartheta_l\sin\phi = z_0\cos\phi \qquad (39)$$

the two-dimensional Fourier transform of this image is:

$$\hat{B}_{1,l_0}(\rho_x, \rho_y, z_0) = \iint dxdy \exp(-2\pi i\rho_x x)\exp(-2\pi i\rho_y y) \times \qquad (40)$$
$$\times \frac{2a_\perp}{\pi a N_p} \sum_m \sum_n \sum_{l=l_0-l}^{l_0+l} \sum_k f(u_i, p_k, \vartheta_l) \times$$
$$\times L(x\cos\vartheta_l + y\sin\vartheta_l - p_k - mw) \times$$
$$\times h(x\sin\vartheta_l\sin\phi - y\cos\vartheta_l\sin\phi + z_0\cos\phi - u_i - nv')$$

Following therefrom with equations (25) and (27):

$$\hat{B}_{1,l_0}(\rho_x, \rho_y, z_0) = \frac{2a_\perp\Delta\rho\Delta\rho_\perp}{\pi a N_p} \sum_l \sum_m \sum_n \times \qquad (41)$$
$$\times \sum_{i=l_0-l}^{l_0+l} \sum_k f(u_i, p_k, \vartheta_l)\exp(-2\pi i m\Delta\rho p_k)\exp(-2\pi i n\Delta\rho_\perp u_i) \times$$
$$\times \exp(2\pi i n\Delta\rho_\perp z_0\cos\phi)\hat{L}(m\Delta\rho)\hat{h}(n\Delta\rho_\perp) \times$$
$$\times \int dx \exp(-2\pi i x(\rho_x - m\Delta\rho\cos\vartheta_l - n\Delta\rho_\perp\sin\vartheta_l\sin\phi)) \times$$
$$\times \int dy \exp(-2\pi i y(\rho_y - m\Delta\rho\sin\vartheta_l + n\Delta\rho_\perp\cos\vartheta_l\sin\phi)) =$$
$$\frac{2a_\perp\Delta\rho\Delta\rho'}{\pi a N_p} \sum_l \sum_m \sum_n \times$$
$$\times \sum_{i=l_0-l}^{l_0+l} \sum_k f(u_i, p_k, \vartheta_l)\exp(-2\pi i m\Delta\rho p_k)\exp(-2\pi i n\Delta\rho_\perp u_i) \times$$
$$\times \exp(2\pi i n\Delta \times \rho_\perp z_0\cos\phi)\hat{L}(m\Delta\rho)\hat{h}(n\Delta\rho_\perp) \times$$
$$\times \delta(\rho_x - m\Delta\rho\cos\vartheta_l - n\Delta\rho_\perp\sin\vartheta_l\sin\phi) \times$$
$$\times \delta(\rho_y - m\Delta\rho\sin\vartheta_l + n\Delta\rho_\perp\cos\vartheta_l\sin\phi)$$

with $\Delta\rho'_\perp = 1/v'$ and—as previously—$\Delta\rho = 1/w$.

When the substitution $$j = i - l_0 \qquad (42)$$

is implemented then based on Equation (4)

$$u_i = u_{j+l_0} = ja_\perp + l_0 a_{195} + du(\vartheta_l) = u_j + l_0 a_\perp \qquad (43)$$

with $$z_0\cos\phi - l_0 a_\perp = dz_0\cos\phi \qquad (44)$$

the following is obtained for $\hat{B}_{1,l_0}(\rho_x, \rho_y, Z_0)$:

$$\hat{B}_{1,l_0}(\rho_x, \rho_y, z_0) = \frac{2a_\perp\Delta\rho\Delta\rho_\perp}{\pi a N_p} \sum_l \sum_m \sum_n \hat{f}_{l0}(n\Delta\rho_\perp, m\Delta\rho, \vartheta_l)\hat{L}(m\Delta\rho)\hat{h}(n\Delta\rho_\perp) \times \qquad (45)$$
$$\times \exp(2\pi i n\Delta\rho_\perp dz_0\cos\phi) \times$$
$$\times \delta(\rho_x - m\Delta\rho\cos\vartheta_l - n\Delta\rho_\perp\sin\vartheta_l\sin\phi) \times$$
$$\times \delta(\rho_y - m\Delta\rho\sin\vartheta_l + n\Delta\rho_\perp\cos\vartheta_l\sin\phi)$$

The term $\hat{f}_{l0}(n\Delta\rho'_\perp, m\Delta\rho, \vartheta_l)$ is thereby the two-dimensional Fourier transform of the projection $f(u_{j+l_0}, p_k, \vartheta_l)$:

$$\hat{f}_{l0}(n\Delta\rho_\perp, m\Delta\rho, \vartheta_l) = \qquad (46)$$
$$\sum_{j=-l}^{l} \sum_k f(j + l_0, k, \vartheta_l)\exp(-2\pi i m\Delta\rho ka)\exp(-2\pi i n\Delta\rho_\perp ja_\perp) \times$$
$$\times \underbrace{\exp(-2\pi i m\Delta\rho(0.5 - a_m)a)\exp(2\pi i n\Delta\rho_\perp du(\vartheta_l))}_{\text{phase factor}}$$

$\hat{B}_{1,l_0}(\rho_x, \rho_y, Z_0)$ in the two-dimensional $\rho_x$–$\rho_y$ frequency space is also defined only at discrete points, namely at the locations $\delta(\rho_x - m\Delta\rho\cos\vartheta_l - n\Delta\rho'_\perp\sin\vartheta_l\sin\phi)$ and $\delta(\rho_y - m\Delta\rho\sin\vartheta_l + n\Delta\rho'_\perp\cos\vartheta_l\sin\phi)$.

This becomes $\delta(\rho_x - m\Delta\rho\cos\vartheta_l)\delta(\rho_y - m\Delta\rho\sin\vartheta_l)$ for $\phi=0$ (projections perpendicularly on the z axis). The points—as in the conventional, two-dimensional case—then lie on a polar grid in the $\rho_x$-$\rho_y$ plane.

In order to make the two-dimensional image $B_{1,l_0}(x, y, z_0)$ ($z_0$ is only a parameter, no longer a variable) useable for the two-dimensional Fourier reconstruction, it is multiplied by the step function $T_1(x) T_1(y)$ (see (20) for definition) and $B_{2,l_0}(X, y, z_0)$, the latter coinciding with $B_{1,l_0}(x, y, z_0)$, in an initially central image excerpt $D_B \cdot D_B$:

$$B_{2,l_0}(x,y,z_0) = B_{1,l_0}(x,y,z_0)T_1(x)T_1(y) \quad (47)$$

The two-dimensional Fourier transform of this image is calculated as:

$$\hat{B}_{2,l_0}(\rho_x, \rho_y, z_0) = \iint dxdy \exp(-2\pi i\rho_x x)\exp(-2\pi i\rho_y y)T_1(x)T_1(y) \times \quad (48)$$

$$\times \frac{2a_\perp}{\pi a N_p} \sum_m \sum_n \sum_{l}^{l} \sum_{j=-l}^{l} \sum_k f(u_{j+l0}, p_k, \vartheta_l) \times$$

$$\times L(x\cos\vartheta_l + y\sin\vartheta_l - p_k - mw) \times$$

$$\times h(x\sin\vartheta_l \sin\phi - y\cos\vartheta_l \sin\phi + z_0\cos\phi - u_{j+l0} - nv') =$$

$$\frac{2a_\perp \Delta\rho\Delta\rho'}{\pi a N_p} \sum_l \sum_m \sum_n \hat{f}_{l0}(n\Delta\rho_\perp, m\Delta\rho, \vartheta_l)\hat{L}(m\Delta\rho)\hat{h}(n\Delta\rho_\perp) \times$$

$$\times \exp(2\pi i n \Delta\rho_\perp dz_0 \cos\phi) \times$$

$$\times \hat{T}_1(\rho_x - m\Delta\rho\cos\vartheta_1 - n\Delta\rho_\perp \sin\vartheta_1\sin\phi) \times$$

$$\times \hat{T}_1(\rho_y - m\Delta\rho\sin\vartheta_1 + n\Delta\rho_\perp \cos\vartheta_1\sin\phi)$$

$\hat{B}_{2,l_0}(\rho_x, \rho_y, Z_0)$ is continuous and—as required for two-dimensional FFT—can be scanned in the Cartesian scan points $\alpha\Delta\rho_x, \beta\Delta\rho_y$, with $$\Delta\rho_x \leq 1/D_B$$

$$\Delta\rho_y \leq 1D_B \quad (49)$$

As in the three-dimensional case, the expansion to non-central image excerpts $D_B \cdot D_B$ in the x-y plane is simple. With $\vec{r}_z = (r_z\cos\vartheta_z, r_z\sin\vartheta_z, 0)$ for the position of the reconstruction center, one obtains:

$$\hat{B}_{z,2,l,0}(\rho_x, \rho_y, z_0) = \frac{2a_\perp\Delta\rho\Delta\rho_\perp}{\pi a N_p} \sum_l \sum_m \sum_n \hat{f}_{l0}(n\Delta\rho_\perp, \quad (50)$$

$$m\Delta\rho, \vartheta_l)\hat{L}(m\Delta\rho)\hat{h}(n\Delta\rho_\perp) \times$$

$$\times \underbrace{\exp(-2\pi i m\Delta\rho_\perp r_z\cos(\vartheta_l - \vartheta_z)) \times}_{\text{phase factor}}$$

$$\times \underbrace{\exp(-2\pi i n\Delta\rho_\perp(r_z\sin\phi\sin(\vartheta_l - \vartheta_z) - dz_0\cos\phi)) \times}_{\text{phase factor}}$$

$$\times \hat{T}_1(\rho_x - m\Delta\rho\cos\vartheta_l - n\Delta\rho_\perp \sin\vartheta_l\sin\phi) \times$$

$$\times \hat{T}_1(\rho_y - m\Delta\rho\sin\vartheta_l + n\Delta\rho_\perp \cos\vartheta_l\sin\phi)$$

The following estimate of the outlay for the reconstruction of an individual slice at $z_0$ is of interest.

As in the three-dimensional reconstruction, the projections that arose given the same projection angle $\vartheta_l$ can be combined for a number of successive $u_j$, so that an effective grid $a_\perp$ having approximately half a slice thickness arises. $l\approx 2$ is then valid, so that the projections $f(u_{j+l0}, p_k, \vartheta_l)$ (given 1024 detector elements) are to be transformed into the frequency space for every projection angle $\vartheta_l$ having a two-dimensional FFT of the length 2048·4. After multiplication by $\hat{L}(m\Delta\rho)\hat{h}(n\Delta\rho_\perp)$ and the corresponding phase factor, each of the supporting points contributes to approximately 4·4 supporting points of the Cartesian grid for the two-dimensional Fourier back-transformation that, as usual, ensues with 1024·1024 values.

A not unsubstantial difference compared to three-dimensional reconstruction lies in the switch to the Cartesian grid: every point therein contributes to 4·4·4 supporting points of the three-dimensional Cartesian grid, a significant advantage.

The total outlay for the production of an individual image should, according to these preliminary estimates, lie at about 3–4 times the outlay for the production of an individual image from conventional, two-dimensional parallel data.

As in the three-dimensional reconstruction, it is easily possible to rotate the two-dimensional discrete slice in space on the basis of a coordinate transformation.

Derivation of $\hat{L}_0(\rho)$:

The relationship $$\hat{L}_0(\rho) = \frac{\pi^2 a^2}{2} |\rho| M_A(\rho)\cos\phi$$

is explained in this section (see Equation (9)).

In continuous notation, the reference image (from Equation (7)) reads:

$$B_0(\vec{r}) = \frac{2}{\pi^2 a^2} \int d\rho \int du \int d\vartheta f(u, p, \vartheta) L_0(\vec{r} \cdot \vec{n}_1 - p) h(\vec{r} \cdot \vec{n} - u) \quad (51)$$

When data are obtained from a uniform circular cylinder having a diameter D and attenuation $\mu$ that has an infinite expanse in the z direction the examination as subject, then $$f(u, p, \vartheta) = \frac{4\mu}{\pi D^2} \frac{2\sqrt{D^2/4 - p^2}}{\cos\phi} \quad (52)$$

is valid, and thus:

$$B_0(\vec{r}) = \quad (53)$$

$$\frac{2}{\pi^2 a^2} \int d\vartheta \int dp \frac{4\mu}{\pi D^2} \frac{2\sqrt{D^2/4 - p^2}}{\cos\phi} L_0(\vec{r} \cdot \vec{n}_1 - p)\underbrace{\int du h(\vec{r} \cdot \vec{n} - u)}_{= \hat{h}=1}$$

With $\vec{r} \cdot \vec{n}_1 = x\cos\vartheta + y\sin\vartheta$, the two-dimensional Fourier transform of the individual slice calculated at an arbitrary location $z_0$ is $$\hat{B}_0(\rho_x, \rho_y, z_0) = \int dx \exp(-2\pi i\rho_x x)\int dy \exp(-2\pi i\rho_y y) \times \quad (54)$$

$$\frac{2}{\pi^2 a^2} \int d\vartheta \int dp \frac{4\mu}{\pi D^2} \frac{2\sqrt{D^2/4 - p^2}}{\cos\phi} L_0(x\cos\vartheta +$$

$$y\sin\vartheta - p) = \int dx \exp(-2\pi i\rho_x x)\int dy \exp(-2\pi i\rho_y y) \times$$

$$\frac{2}{\pi^2 a^2} \int d\rho \int d\vartheta \int dp \frac{4\mu}{\pi D^2} \frac{2\sqrt{D^2/4 - p^2}}{\cos\phi} \times$$

$$\times \hat{L}_0(\rho)\exp(2\pi i\rho(x\cos\vartheta + y\sin\vartheta - p))$$

Because $$\int dx \exp(-2\pi ix(\rho_x - \rho\cos\vartheta)) = \delta(\rho_x - \rho\cos\vartheta) = \delta(\rho_x - \rho_x) \quad (55)$$

$$\int dy \exp(-2\pi iy(\rho_y - \rho\sin\vartheta)) = \delta(\rho_y - \rho\sin\vartheta) = \delta(\rho_y - \rho_y) \quad (56)$$

and $$|\rho| d\rho d\vartheta = d\rho'_x d\rho'_y \quad (57)$$

one can thus write:

$$\hat{B}_0(\rho_x, \rho_y, z_0) = \frac{2}{\pi^2 a^2} \int d\rho \frac{4\mu}{\pi D^2} \frac{2\sqrt{D^2/4 - p^2}}{\cos\phi} \exp(-2\pi i \rho p) \frac{\hat{L}_0(\rho)}{|\rho|} \quad (58)$$

$$\frac{2}{\pi^2 a^2} \mu \frac{J_1(\pi\rho D)}{\pi\rho D} \frac{\hat{L}_0(\rho)}{|\rho|\cos\phi}$$

With $M_A(\rho)$ as a modulation transfer function and $\hat{O}(\rho)$ as the two-dimensional Fourier transform into the $\rho_x$-$\rho_y$ plane of the circular cylinder with infinite expanse in the z direction, the following is simultaneously valid:

$$\hat{B}_0(\rho_x, \rho_y, z_0) = \hat{O}(\rho) M_A(\rho) = \mu \frac{J_1(\pi\rho D)}{\pi\rho D} M_A(\rho) \quad (59)$$

Following therefrom, $$\hat{L}_0(\rho) = \frac{\pi^2 a^2}{2} |\rho| M_A(\rho) \cos\phi \quad (60)$$

Figure 5:
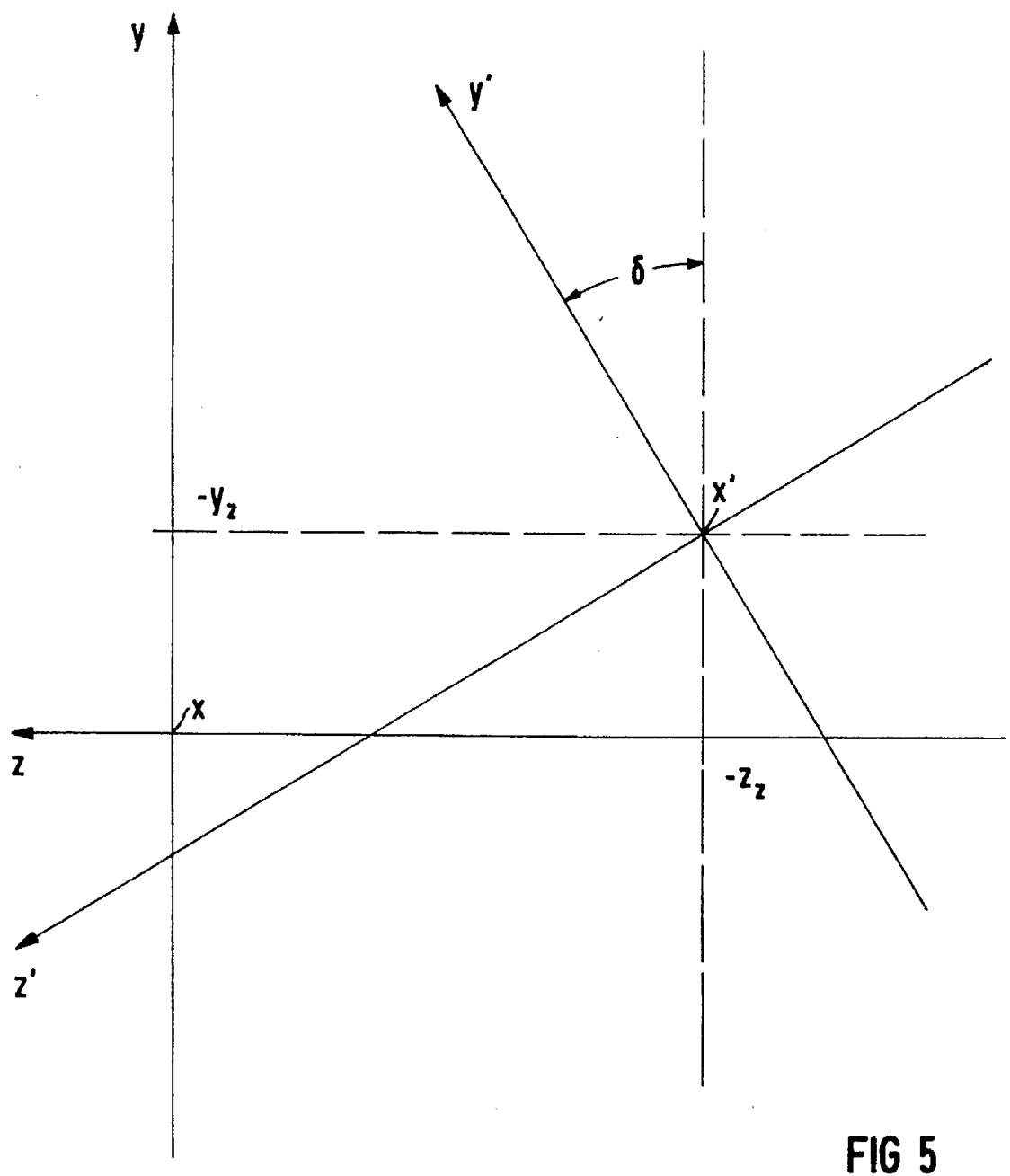

Coordinate Transformation and Derivation of the Reconstruction Equations for Arbitrarily Rotated, Individual Slices:

FIG. 5 illustrates the first step of the coordinate transformation. The starting point is the coordinate system x, y, z. The new coordinate system x', y', z' is shifted $(-x_z, -y_z, -z_z)$ and is rotated by the angle $\delta$. The x' axis is the rotational axis. Thus $$x' = x + x_z \quad (61)$$

$$y' = (Y + y_z)\cos\delta + (z + z_z)\sin\delta \quad (62)$$

$$z' = -(y + y_z)\sin\delta + (z + z_z)\cos\delta \quad (63)$$

The coordinate system x', y', z' is subsequently rotated by the angle $\gamma$. The y' axis is the rotational axis. The coordinate system x", y", z" is obtained with $$x'' = x'\cos\gamma + z'\sin\gamma \quad (64)$$

$$z'' = -x'\sin\gamma + z'\cos\gamma \quad (65)$$

$$y'' = y' \quad (66)$$

The overall transformations are:

$$x = x''\cos\gamma - z''\sin\gamma - x_z \quad (67)$$

$$y = y''\cos\delta - x''\sin\gamma\sin\delta - z''\cos\gamma\sin\delta - y_z \quad (68)$$

$$z = x''\sin\gamma\cos\delta + z''\cos\gamma\cos\delta + y''\sin\delta - z_z \quad (69)$$

The individual slice in the coordinate system x", y", z" is observed at the location z"=0 (otherwise, $x_z$, $y_z$, $z_z$ could have been differently selected). Then $$x = x''\cos\gamma - x_z \quad (70)$$

$$y = y''\cos\delta - x''\sin\gamma\sin\delta - y_z \quad (71)$$

$$z = x''\sin\gamma\cos\delta + y''\sin\delta - z_z \quad (72)$$

The starting point for the image description is equation (37):

$$B_{1,l_0}(x, y, z) = \frac{2a_\perp}{\pi a N_p} \sum_m \sum_n \sum_l \sum_{i=l_0-l}^{l_0+l} \sum_k f(u_i, p_k, \vartheta_l) \times \quad (73)$$

$\times L(x\cos\vartheta_l + y\sin\vartheta_l - p_k - mw) \times$ $\times h(x\sin\vartheta_l\sin\phi - y\cos\vartheta_l\sin\phi + z\cos\phi - u_i - nv')$ Following therefrom with Equations (10), (11), (12):

$$B_{1D,l_0}(x'', y'', 0) = \frac{2a_\perp}{\pi a N_p} \sum_m \sum_n \sum_l \sum_{i=l_0-l}^{l_0+l} \sum_k f(u_i, p_k, \vartheta_l) \times \quad (74)$$

$\times L(x''\cos\vartheta_l\cos\gamma - x_z\cos\vartheta_l + y''\sin\vartheta_l\cos\delta - x''\sin\vartheta_l\sin\gamma\sin\delta -$ $y_z\sin\vartheta_l - p_k - mw) \times h(x''\sin\vartheta_l\sin\phi\cos\gamma - x_z\sin\vartheta_l\sin\phi -$ $y''\cos\vartheta_l\sin\phi\cos\delta + x''\cos\vartheta_l\sin\phi\sin\gamma\sin\delta +$ $+ y_z\cos\vartheta_l\sin\phi + x''\cos\phi\sin\gamma\cos\delta + y''\cos\phi\sin\delta - z_z\cos\phi - u_i - nv')$ The two-dimensional Fourier transform with respect to x" and y" at the location z"=0 is $$\hat{B}_{1D,l_0}(\rho_{x''}, \rho_{y''}, 0) = \frac{2a_\perp \Delta\rho \Delta\rho_\perp}{\pi a N_p} \sum_m \sum_n \sum_l \sum_{i=l_0-l}^{l_0+l} \sum_k \times \quad (75)$$

$\times f(u_i, p_k, \vartheta_l) \exp(-2\pi i m \Delta\rho p_k) \exp(-2\pi i n \Delta\rho_\perp u_i) \hat{L}(m\Delta\rho) \hat{h}(n\Delta\rho_\perp) \times$ $\times \exp(-2\pi i m \Delta\rho(x_z\cos\vartheta_l + y_z\sin\vartheta_l)) \times$ $\times \exp(-2\pi i n \Delta\rho_\perp(x_z\sin\vartheta_l\sin\phi - y_z\cos\vartheta_l\sin\phi + z_z\cos\phi)) \times$ $\times \delta(\rho_{x''} - m\Delta\rho(\cos\vartheta_l\cos\gamma - \sin\vartheta_l\sin\gamma\sin\delta) -$ $- n\Delta\rho_\perp(\sin\vartheta_l\sin\phi\cos\gamma + \cos\vartheta_l\sin\phi\sin\gamma\sin\delta + \cos\phi\sin\gamma\cos\delta)) \times$ $\times \delta(\rho_{y''} - m\Delta\rho\sin\vartheta_l\cos\delta + n\Delta\rho_\perp(\cos\vartheta_l\sin\phi\cos\delta - \cos\phi\sin\delta))$ with the substitution $$j = i - l_0 \quad (76)$$

$$u_i = u_j + l_0 a_\perp = j a_\perp + l_0 a_\perp + du(\vartheta_l) = u_j + l_0 a_\perp \quad (77)$$

$$-z_z\cos\phi - l_0 a_\perp = dz_0\cos\phi \quad (78)$$

this becomes $$\hat{B}_{1D,l_0}(\rho_{x''}, \rho_{y''}, 0) = \quad (79)$$

$$\frac{2a_\perp \Delta\rho \Delta\rho_\perp}{\pi a N_p} \sum_m \sum_n \sum_l \hat{f}_{l_0}(n\Delta\rho_\perp, m\Delta\rho, \vartheta_l) \hat{L}(m\Delta\rho) \hat{h}(n\Delta\rho_\perp) \times$$

$\times \exp(-2\pi i m \Delta\rho(x_z\cos\vartheta_l + y_z\sin\vartheta_l)) \times$ $\times \exp(-2\pi i n \Delta\rho_\perp(x_z\sin\vartheta_l\sin\phi - y_z\cos\vartheta_l\sin\phi - dz_0\cos\phi)) \times$ $\times \delta(\rho_{x''} - m\Delta\rho(\cos\vartheta_l\cos\gamma - \sin\vartheta_l\sin\gamma\sin\delta) -$ $- n\Delta\rho_\perp(\sin\vartheta_l\sin\phi\cos\gamma + \cos\vartheta_l\sin\phi\sin\gamma\sin\delta + \cos\phi\sin\gamma\cos\delta)) \times$ $\times \delta(\rho_{y''} - m\Delta\rho\sin\vartheta_l\cos\delta + n\Delta\rho_\perp(\cos\vartheta_l\sin\phi\cos\delta - \cos\phi\sin\delta))$ $\hat{f}_{l_0}(n\Delta\rho_\perp, m\Delta\rho, \vartheta_l)$ is the two-dimensional Fourier transform of $f(u_{j+l_0}, p_k, \vartheta_l)$:

$$\hat{f}_{l_0}(n\Delta\rho_\perp, m\Delta\rho, \vartheta_l) = \quad (80)$$

$$\sum_{j=-l}^{l} \sum_k f(j + l_0, k, \vartheta_l) \exp(-2\pi i m \Delta\rho k a) \exp(-2\pi i n \Delta\rho_\perp j a_\perp) \times$$

-continued $$\times \exp(-2\pi i m \Delta \rho (0.5 - a_m)a) \exp(2\pi i n \Delta \rho_\perp du(\vartheta_l))$$

The image $B_{1D,l_0}(x'', y'', 0)$ is multiplied by the step function $T_1(x'')$, $T_1(y'')$ in the new coordinate system $x''$, $y''$, $z''$ and the image $B_{2D,l_0}(x'', y'', 0)$ is obtained with the Fourier transform $$\hat{B}_{2D,l_0}(\rho_{x''}, \rho_{y''}, 0) = \tag{80}$$

$$\frac{2a_\perp \Delta \rho \Delta \rho_\perp}{\pi a N_p} \sum_m \sum_n \sum_l \hat{f}_{l_0}(n\Delta \rho_\perp, m\Delta \rho, \vartheta_l) \hat{L}(m\Delta \rho) \hat{h}(n\Delta \rho_\perp) \times$$

$$\times \exp(-2\pi i m \Delta \rho (x_z \cos \vartheta_l + y_z \sin \vartheta_l)) \times$$

$$\times \exp(-2\pi i n \Delta \rho_\perp (x_z \sin \vartheta_l \sin \varphi - y_z \cos \vartheta_l \sin \varphi - dz_0 \cos \varphi)) \times$$

$$\times \hat{T}_1(\rho_{x''} - m\Delta \rho (\cos \vartheta_l \cos \gamma - \sin \vartheta_l \sin \gamma \sin \delta) -$$

$$- n\Delta \rho_\perp (\sin \vartheta_l \sin \varphi \cos \gamma + \cos \vartheta_l \sin \varphi \sin \gamma \sin \delta + \cos \varphi \sin \gamma \cos \delta)) \times$$

$$\times \hat{T}_1(\rho_{y''} - m\Delta \rho \sin \vartheta_l \cos \delta + n\Delta \rho_\perp (\cos \vartheta_l \sin \varphi \cos \delta - \cos \varphi \sin \delta))$$

The sole difference compared to equation (50) is that the weighting functions $\hat{T}_1(\rho_{x''})$ $\hat{T}_1(\rho_{y''})$ are to be calculated at other locations because of the rotated coordinate system. This, however, does not involve added outlay because $\gamma$ and $\delta$ are constants. Added outlay does arise, however, because individual scans must be utilized for constructing a slice under certain circumstances, i.e. l becomes larger.

When $\delta=0$ and $\gamma=0$ is set, equation (50) is obtained.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray computed tomography apparatus comprising:

an annular x-ray source containing a ring anode surrounding a measuring field and means for scanning said ring electrode with an electron beam for producing an x-ray beam rotating around said measuring field through successive projection angles $\vartheta_l$ in a plane inclined at an angle $\phi$ relative to an x-y plane of a Cartesian coordinate system having an origin, said x-y plane being disposed a distance $z_i$ from said origin;

means for operating said annular x-ray source for conducting a scan in parallel beam geometry of an examination subject disposed in said measuring field by irradiating said examination subject with said x-ray beam once from each of said successive projection angles $\vartheta_l$;

radiation detector means for detecting said x-ray beam during said scan after passing through said examination subject from each of said projection angles $\vartheta_l$ to obtain a set of measured values $f(u_i, p_k, \phi_l)$ for each scan for each projection angle $\vartheta_l$ and each position $u_i = z_i/\cos\phi$ and each position $p_k$ in a selected direction from the z-axis of said Cartesian coordinate system;

means for generating a representation of a volume image of said examination subject from said set of measured data by two-dimensionally Fourier transforming said set of measured data with respect to $u_i$ and $p_k$ to obtain a frequency space function, multiplying said frequency space function by an interpolation function in one dimension of said frequency space and by a convolution core function in another dimension of said frequency space to obtain an interpolated, convoluted product, multiplying said interpolated, convoluted product by a phase factor which is dependent on a location of each point of said interpolated, convoluted product relative to a reconstruction volume in a locus space to obtain a final set of frequency space points, three-dimensionally gridding said final set of frequency space points onto points of a three-dimensional Cartesian grid with grid dimensions $\Delta\rho_x$, $\Delta\rho_y$ and $\Delta\rho_z$, freely selecting $\Delta\rho_x$, $\Delta\rho_y$ and $\Delta\rho_z$ to generate an arbitrarily selected excerpt of said representation of said volume image, and by three-dimensionally fast Fourier transforming said arbitrarily selected excerpt into said locus space; and means for displaying the arbitrarily selected excerpt transformed into said locus space.

2. An x-ray computed tomography apparatus comprising:

an annular x-ray source containing a ring anode surrounding a measuring field and means for scanning said ring electrode with an electron beam for producing an x-ray beam rotating around said measuring field through successive projection angles $\vartheta_l$ in a plane inclined at an angle $\phi$ relative to an x-y plane of a Cartesian coordinate system having an origin, said x-y plane being disposed a distance $z_i$ from said origin;

means for operating said annular x-ray source for conducting a scan in parallel beam geometry of an examination subject disposed in said measuring field by irradiating said examination subject with said x-ray beam once from each of said successive projection angles $\vartheta_l$;

radiation detector means for detecting said x-ray beam during said scan after passing through said examination subject from each of said projection angles $\vartheta_l$ to obtain a set of measured values $f(u_i, p_k, \phi_l)$ for each scan for each projection angle $\vartheta_l$ and each position $u_i = z_i/\cos\phi$ and each position $p_k$ in a selected direction from the z-axis of said Cartesian coordinate system;

means for generating a representation of a planar image of said examination subject from said set of measured data by two-dimensionally Fourier transforming said set of measured data with respect to $u_i$ and $p_k$ to obtain a frequency space function, multiplying said frequency space function by an interpolation function in one dimension of said frequency space and by a convolution core function in another dimension of said frequency space to obtain an interpolated, convoluted product, multiplying said interpolated, convoluted product by a phase factor which is dependent on a location of each point of said interpolated, convoluted product relative to a reconstruction volume in a locus space to obtain a final set of frequency space points, two-dimensionally gridding said final set of frequency space points onto points of a two-dimensional Cartesian grid with grid dimensions $\Delta\rho_x$, and $\Delta\rho_y$, freely selecting $\Delta\rho_x$ and $\Delta\rho_y$ to generate an arbitrarily selected excerpt of said planar image, two-dimensionally fast Fourier transforming said arbitrarily selected excerpt into said locus space and directly fast Fourier transforming said final set of frequency space points for z=0 into said locus space; and means for displaying said arbitrarily selected excerpt transformed into said locus space.

\* \* \* \* \*